United States Patent
Zajac

(10) Patent No.: US 10,335,283 B2
(45) Date of Patent: Jul. 2, 2019

(54) REVERSE HIP SYSTEM AND METHOD

(71) Applicant: Tyler J Zajac, Livonia, MI (US)

(72) Inventor: Tyler J Zajac, Livonia, MI (US)

(*) Notice: Subject to any disclaimer, the term of this patent is extended or adjusted under 35 U.S.C. 154(b) by 64 days.

(21) Appl. No.: 15/867,221

(22) Filed: Jan. 10, 2018

(65) Prior Publication Data

US 2018/0193156 A1 Jul. 12, 2018

Related U.S. Application Data

(60) Provisional application No. 62/444,451, filed on Jan. 10, 2017.

(51) Int. Cl.
| | |
|---|---|
| *A61F 2/32* | (2006.01) |
| *A61F 2/36* | (2006.01) |
| *A61F 2/34* | (2006.01) |
| *A61F 2/30* | (2006.01) |
| *A61F 2/46* | (2006.01) |

(52) U.S. Cl.
CPC ........ *A61F 2/3609* (2013.01); *A61F 2/30771* (2013.01); *A61F 2/32* (2013.01); *A61F 2/34* (2013.01); *A61F 2/367* (2013.01); *A61F 2/4609* (2013.01); *A61F 2/30749* (2013.01); *A61F 2002/3092* (2013.01); *A61F 2002/3093* (2013.01); *A61F 2002/30332* (2013.01); *A61F 2002/30411* (2013.01); *A61F 2002/30433* (2013.01); *A61F 2002/30616* (2013.01); *A61F 2002/30663* (2013.01); *A61F 2002/30673* (2013.01); *A61F 2002/30784* (2013.01); *A61F 2002/30878* (2013.01); *A61F 2002/3401* (2013.01); *A61F 2002/3404* (2013.01); *A61F 2002/345* (2013.01); *A61F 2002/3408* (2013.01); *A61F 2002/3411* (2013.01); *A61F 2002/3448* (2013.01); *A61F 2002/3483* (2013.01); *A61F 2002/365* (2013.01); *A61F 2002/3615* (2013.01); *A61F 2002/3654* (2013.01); *A61F 2002/4629* (2013.01); *A61F 2310/00796* (2013.01)

(58) Field of Classification Search
CPC .. A61F 2/32; A61F 2/3609; A61F 2/34; A61F 2/367

See application file for complete search history.

(56) References Cited

U.S. PATENT DOCUMENTS

| 5,080,685 A | 1/1992 | Bolesky et al. |
|---|---|---|
| 8,313,531 B2 | 11/2012 | Termanini |
| 8,465,549 B2 | 6/2013 | Richardson |
| 2010/0174380 A1 | 7/2010 | Lewis |

*Primary Examiner* — Jason-Dennis N Stewart
(74) *Attorney, Agent, or Firm* — Carrier Blackman & Associates, P.C.; Joseph P. Carrier; William D. Blackman

(57) ABSTRACT

A reverse hip prosthesis include an acetabular cup arrangement configured for insertion into an acetabulum of a patient and fixation therein, an acetabular ball configured for threaded attachment to the acetabular cup arrangement, a femoral stem configured for insertion into an intramedullary femoral canal of the patient, and a femoral cup arrangement configured for attachment to the femoral stem and to operatively receive the acetabular ball therein. The acetabular cup arrangement includes an anchor portion which becomes fixed to the patient's acetabulum and is the largest size suitable for the patient, and an insert which comes in different sizes and are connectable to the anchor portion, so that the most appropriate insert for the patient may be used. The acetabular cup arrangement and ball are interconnected with a threaded stem that also functions as an artificial Ligamentum Teres.

20 Claims, 6 Drawing Sheets

REVERSE HIP SYSTEM AND METHOD

CROSS-REFERENCE TO RELATED APPLICATIONS

The present application claims the benefit of priority to U.S. Provisional Patent Application No. 62/444,451, filed Jan. 10, 2017. The entire subject matter of these priority documents, including specification claims and drawings thereof, is incorporated by reference herein.

TECHNICAL FIELD

The present disclosure relates to an improved reverse hip system and method. More particularly, the present disclosure relates to such a system and method with improved adjustability to assure best fitment for each individual patient, maximized stability and joint range of motion, and facilitated repair—replacement should the same become necessary.

BACKGROUND

Despite advances in designs, materials, and techniques, hip replacements may still fail, or otherwise require revision, much earlier than desired. In response to this, improvements continue to be made to increase the longevity of hip replacement systems. Some hip replacement systems are "anatomic" in design, i.e., the head of the patient's femur is replaced with a partially spherical ball attached to a stem that is affixed to the femur, and on the other side of the joint a partially spherical cup is affixed to the patient's acetabulum to provide a wear surface for the replacement femoral ball. Other designs provide a reverse configuration from the anatomic design described above. More particularly, the articulating ball portion of the hip replacement system is attached on the acetabular side of the joint, while the cup in which the ball articulates is attached to the femoral side of the joint. Various hip replacement systems and methods are described in the following patent references: U.S. Pat. No. 8,465,549B2, U.S. Pat. No. 8,313,531 B2, U.S. Pat. No. 5,080,685A, and US20100174380A1.

SUMMARY

At least some embodiments described herein may include a reverse hip prosthesis that includes an acetabular cup arrangement configured for insertion into an acetabulum of a patient and fixation therein. An acetabular ball may be configured for threaded attachment to the acetabular cup arrangement, and a femoral stem may be configured for insertion—fixation into an intramedullary femoral canal of the patient. A femoral cup arrangement may be configured for attachment to the femoral stem and to operatively receive the acetabular ball therein such that the femoral cup and the acetabular ball may rotate—articulate relative to each other. The first portion will have substantially a largest size suitable—acceptable for the patient, while several versions of the second portion will be provided in several different sizes in terms of depth and/or wall thickness so that an appropriate size insert may be selected/used for the patient.

In accordance with at least some embodiments described herein, the acetabular cup arrangement includes an anchor portion configured to be directly fixed to the acetabulum of the patient and an insert configured for insertion into and fixation with the anchor portion. The anchor portion may have substantially a largest size suitable—acceptable for the patient, while the insert will be provided in several different sizes in terms of depth, wall thickness, etc. so that a most appropriate size insert may be selected/used for the patient. The insert may be formed of wearable material(s) including polymers such as high density polyethylene (HDPE), high molecular weight polyethylene (HMWPE) or other suitable materials, and may include a self-lubricating material provided at at least a surface thereof.

In accordance with at least some embodiments described herein, the acetabular cup arrangement includes a first or anchor portion configured to be directly fixed to the acetabulum of the patient, a second portion configured for insertion into and fixation with the first portion and an insert configured for insertion into and fixation with the second portion. The second portion will be provided in several different sizes in terms of depth, wall thickness, etc. so that a most appropriate size second portion may be selected/used for the patient. The insert may be formed of wearable material(s) including polymers such as high density polyethylene (HDPE), high molecular weight polyethylene (HMWPE) or other suitable materials, and may include a self-lubricating material provided at at least a surface thereof.

In accordance with at least some embodiments described herein, a femoral cup arrangement includes a femoral cup configured for attachment to a femoral stem, and further configured to receive a polymeric insert therein. The polymeric insert may be, for example, have a lip or flange that may be snap-fitted into/onto a groove, annular projection or other geometric configuration of the femoral cup, or may be attached by other ways effective to create the desired fit. The femoral cup arrangement may be attached to the femoral stem, for example, by a Morse taper, wherein the female portion of the taper is on the femoral cup or the femoral stem. The femoral cup arrangement may also be attached to the femoral stem by other mechanisms, for example, by a threaded attachment. The femoral cup may have a projection, recess and/or other appropriate device provided on an outer surface thereof which may be used for facilitating removal of the femoral cup from the femoral stem should it become necessary to do so.

In accordance with at least some embodiments described herein, the acetabular cup arrangement and the acetabular ball may be interconnected by a threaded member that also functions as an artificial Ligamentum Teres.

DETAILED DESCRIPTION

As required, detailed, exemplary embodiments of the present invention are disclosed herein. However, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
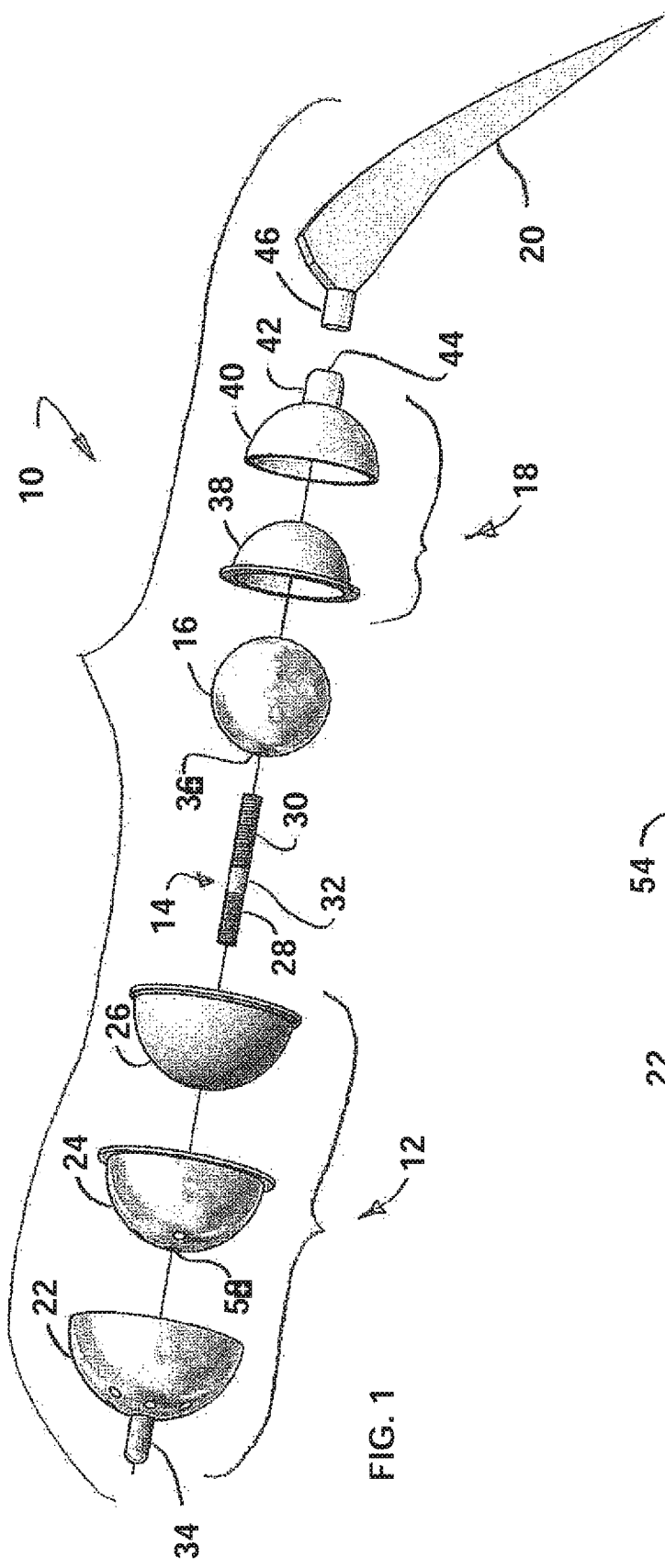
FIG. 1 shows an exploded view of a reverse prosthesis hip system in accordance with an exemplary embodiment described herein.

FIG. 1 shows a reverse prosthesis hip system 10 in accordance with an exemplary embodiment described herein. The system 10 includes an acetabular cup arrangement 12, a threaded stem 14, an acetabular ball 16, a femoral cup arrangement 18, and a femoral stem 20. Specific features of each of these components are described in more detail below in conjunction with associated drawing figures. The acetabular cup arrangement 12 includes: a first portion 22 which may be conveniently referred to as an anchor portion because it is configured to be inserted directly into the patient's acetabulum and firmly affixed thereto; a second portion or acetabular cup 24 configured for insertion into the anchor portion 22; an insert 26 configured for insertion into and attachment to the acetabular cup 24, and may be, for example, snap fit, or affixed in any way that is effective to provide the desired fixation between the insert 26 and the acetabular cup 24; and a threaded stem 14 which may be used to secure the acetabular cup 24 to the anchor portion 22. The acetabular cup arrangement components and the femoral cup arrangement of the system 10 may be locking or non-interlocking.

In the embodiment shown in FIG. 1, the threaded stem 14 includes first and second threaded portions 28, 30 separated by a non-threaded shoulder 32. The first threaded portion 28 is configured to mate with female threads on the inside of a stem 34 disposed on a proximal side of the anchor portion 22 which is inserted directly into the patient's acetabulum and firmly affixed thereto. The length of the first threaded portion 28 and the diameter of the shoulder 32 can be configured so that the acetabular cup 24, and if desired the insert 26—are held firmly in place when the threaded stem 14 is screwed into the anchor stem 34. More particularly, by providing the first threaded portion 28 with a length that is less than a length of the internal threaded portion of the anchor stem 34, and by providing the shoulder 32 with a larger diameter than a diameter of the threads, the threaded stem 14 may act as a threaded fastener to hold the components of the acetabular cup arrangement 12 in place.

The acetabular ball 16 includes a threaded hole 36 configured to mate with the second threaded portion 30 on the threaded stem 14. Similar to the design of the first threaded portion 28, the second threaded portion 30 can be provided with a length that is less than a length of the internal threaded portion of the hole 36 such that the acetabular ball 16 "bottoms-out" securely on the shoulder 32 of the threaded stem 14. The acetabular ball 16 is configured to articulate within an insert 38, which forms a portion of the femoral cup arrangement 18. The insert 38 is configured to mate with a femoral cup 40 of the femoral cup arrangement 18. The insert 38 may be configured to snap-fit into/onto the femoral cup 40, or to be attached by any other means effective to provide the desired fixation. In the embodiment shown in FIG. 1, the femoral cup 40 includes a stem 42 in which there is a female Morse taper 44—see also FIG. 6—that is configured to mate with a neck 46 having a male Morse taper and which is disposed on a proximal end of the femoral stem 20.

Figure 2A:
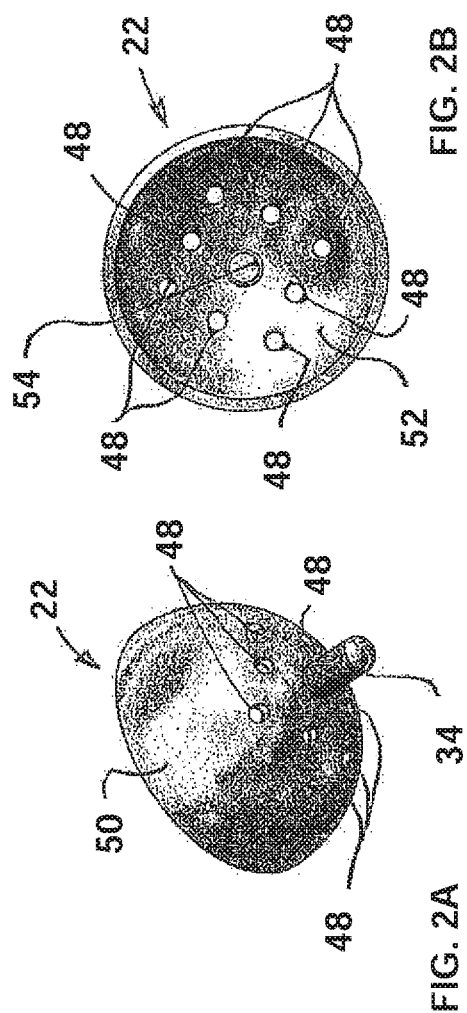
FIGS. 2A-2B show different views of a portion of an acetabular cup arrangement that is part of the hip system shown in FIG. 1.
Figure 2B:
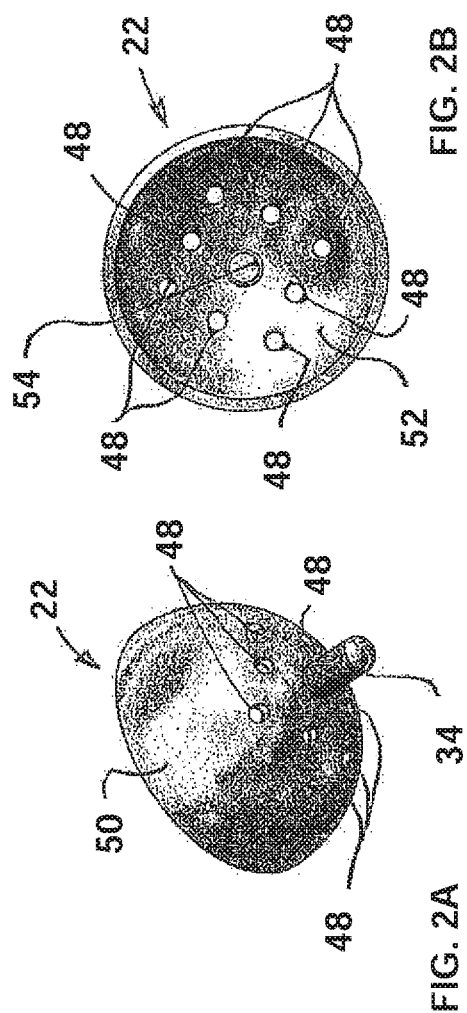
Figure 11:
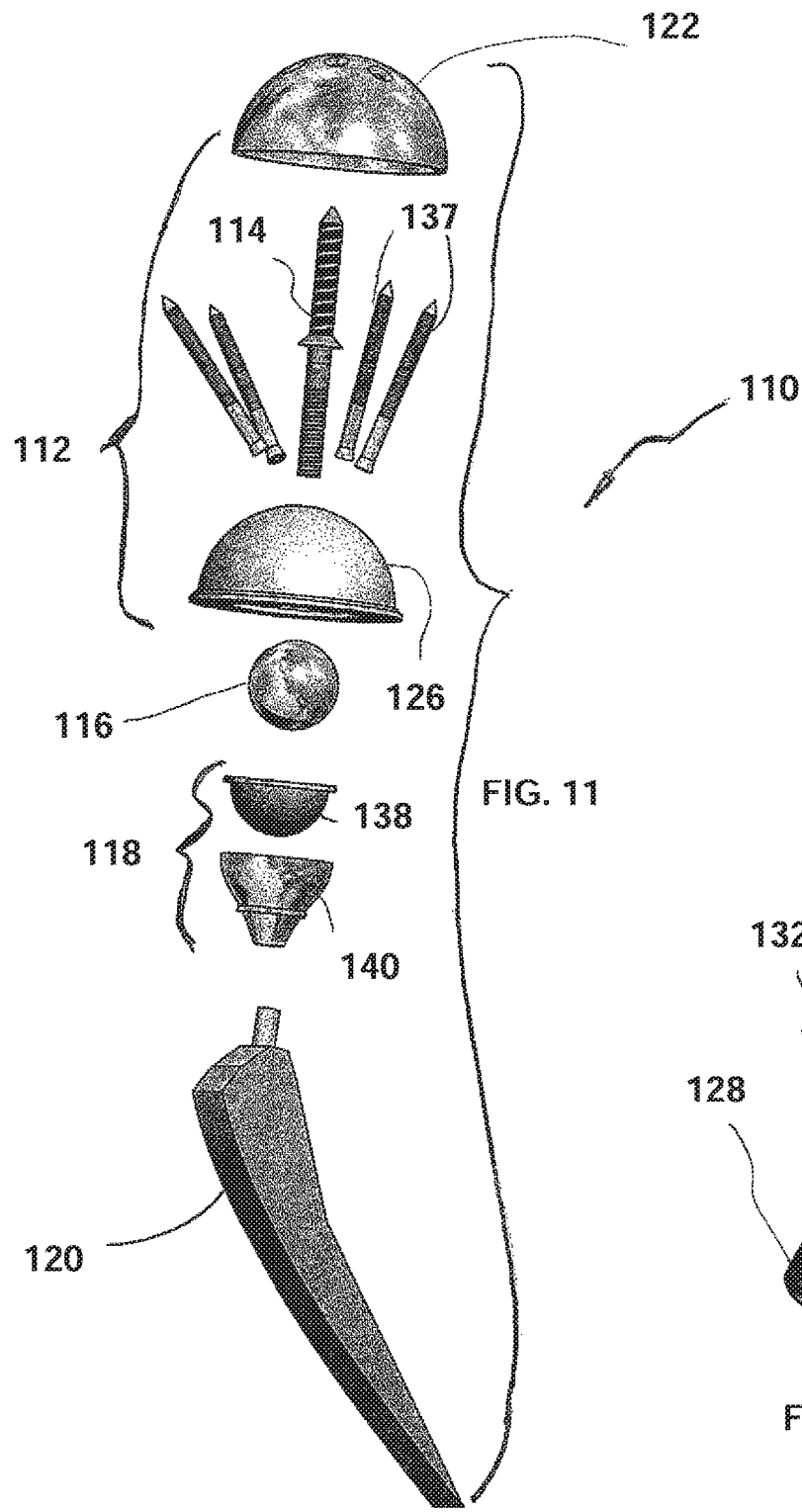
FIG. 11 shows an exploded view of a reverse prosthesis hip system in accordance with another exemplary embodiment described herein.

FIG. 2A shows a perspective view of the first or anchor portion 22 of the acetabular cup arrangement 12, while FIG. 2B shows an inside surface 52 of the anchor portion 22, including a threaded hole 54 disposed on the inside of the stem 34 which receives the first threaded portion 28 of the threaded stem 14. As shown in FIG. 2A, the anchor portion 22 includes a plurality of holes 48, eight holes 48 are depicted in this embodiment, through which bone screws or other appropriate fasteners may pass for affixing the anchor portion 22 to a patient's acetabulum. Exemplary bone screws 137 are shown in FIG. 11. The bone screws will have heads sized such that they will not pass through the holes 48. Alternatively, or in conjunction with the bone screws or other fasteners, some or all of an outside surface 50 of the anchor portion 22 may be configured for bone ingrowth, e.g., it may be porous coated, coated with hydroxyapatite, plasma-spray coated, it may have other geometric configurations, or it may have some combination of one or more of these. As described above, the hole 54 is configured to permit passage the first threaded portion 28 of the threaded stem 14, and such hole 54 may be surrounded by the holes 48 so that a suitable number of the bone screws may be extended through appropriate ones of the holes 48. See also FIGS. 1, 11. In the embodiment shown in FIG. 11 four of the bone screws 137 are used.

Figure 3A:
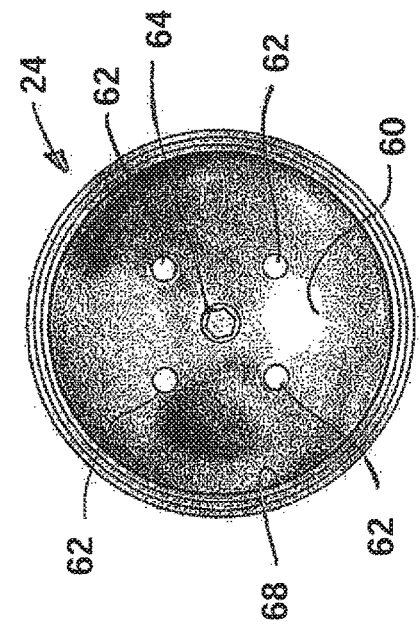
FIGS. 3A-3B show different views of another portion of the acetabular cup arrangement shown in FIG. 1.
Figure 3B:
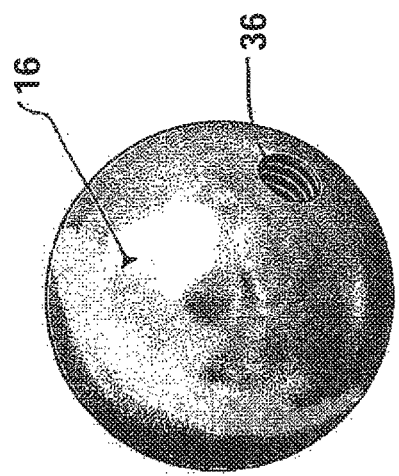

FIG. 3A shows a perspective view of the second portion 24, or acetabular cup, of the acetabular cup arrangement 12 having the threaded stem 14 extended through a central opening 58 defined through a center of the acetabular cup 24, while FIG. 3B shows an inner or distal surface 60 of the acetabular cup 24, and also shows a number of holes 62 (four are depicted) defined through the cup 24 in an appropriate pattern surrounding the center opening 58 so that the holes 62 may be aligned with some or all of the holes 48 in the anchor portion 22 to permit the bone screws to be inserted through aligned holes of the acetabular cup 24 and the anchor portion 22 in order to affix both of these components firmly to the patient's acetabulum. As shown in FIG. 3A, most or all of the first threaded portion 28 of the threaded stem 14 extends outward from a proximal surface 56 of the acetabular cup 24 after the threaded stem 14 has been disposed through the center hole 58 of the acetabular cup 24. The center hole 58 may be threaded to mate with the first threaded portion 28, or alternatively, it may be unthreaded and allow the threaded stem 14 to pass through with only minor interference. In such a configuration, it may be convenient to ensure that the hole 58 has a diameter that is smaller than a diameter of the shoulder 32 of the threaded stem 14 so that the shoulder 32 may secure the acetabular cup 24 to the anchor portion 22. The acetabular cup 24 may include an annular flange 68 which is configured to be securely connected to a lip 66 of the insert 26 as discussed further herein.

As shown in FIG. 3B, a distal end 64 of the threaded stem 14 may include an hexagonal socket or the like defined therein so that a hexagonal wench or other appropriate tool can be inserted for tightening the threaded stem 14 into the internal threads of the stem 34 of the anchor portion 22. In other embodiments, a threaded stem, such as the threaded stem 14, may have other tool-attachment features, such as a square hole, a slot, a Philips-head, a hexalobular internal configuration, often called a star- or Torx-head configuration, etc.

Figure 4A:
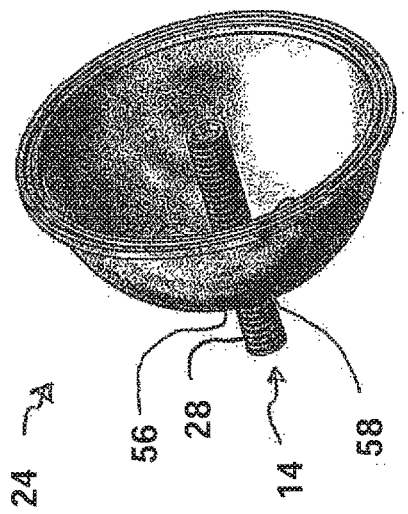
FIGS. 4A-4B show an insert that can be used with the acetabular cup arrangement shown in FIG. 1.
Figure 4B:
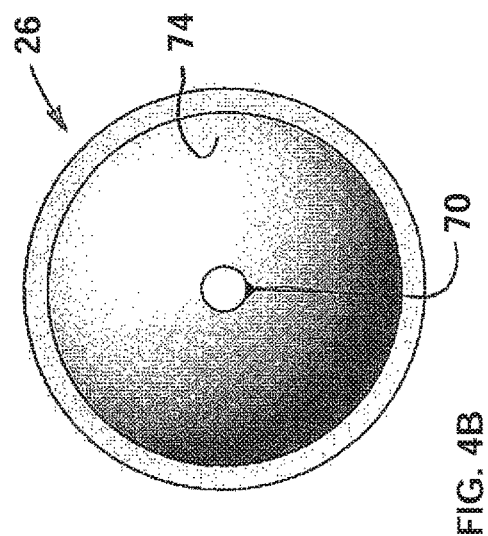

FIGS. 4A, 4B respectively show a perspective view and an end view of the insert 26. As shown, the insert 26 includes proximal surface 72, inner or distal surface 74 and the lip 66 disposed around a circumferential edge thereof. The lip 66 may be configured to achieve a snap-fit with a mating internal feature of the annular flange 68 of the acetabular cup 24 which is shown in FIGS. 3A, 3B, e.g., the annular flange 68 may have an annular recess at a radially intermediate portion thereof and the lip 66 may have an annular projection which securely engages within the annular recess via snap fit. As shown in FIG. 4A, the insert 26 includes a hole 70 defined through a center thereof, which aligns with center opening 58 in the acetabular cup 24 and is sized and configured to receive the first threaded portion 28 of the threaded stem 14 therethrough. The hole 70 may be large enough for the threaded stem 14 to pass through without interference, or alternatively, it may be sized to have a diameter smaller than the diameter of the shoulder 32 of the threaded stem 14 so that the shoulder 32 may impose a force on to the insert 26 to help keep it in place when the first threaded portion 28 of the threaded stem 14 is engaged with the anchor stem 34.

FIG. 4B shows the proximal or inside surface 74 of the insert 26. In the system 10 shown in FIG. 1 the acetabular cup 24 is provided in various sizes so that a most appropriate size for any given patient may be used, and the insert 26 is securely fitted to the acetabular cup 24. Thus, the inside surface 74 conforms to the to the shape of the inside surface 60 of the acetabular cup 24 and will be sized appropriately to allow the femoral cup arrangement 18 to articulate around the acetabular ball 16 when the system 10 is fully assembled and installed on the patient. More specifically, the inside surface 60 of the acetabular cup 24, and the inside surface 74 of the insert fitted to the cup, may have a radius that is larger than a radius of the acetabular ball 16 so that there is no impingement between the femoral cup arrangement 18 and the insert 26 when the system 10 is in use.

Figure 5A:
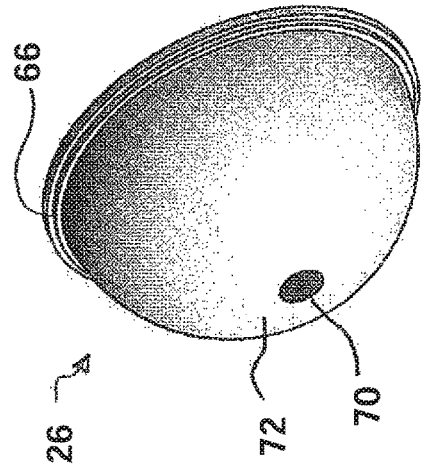
FIGS. 5A-5B show an acetabular ball that is part of the system shown in FIG. 1.
Figure 5B:
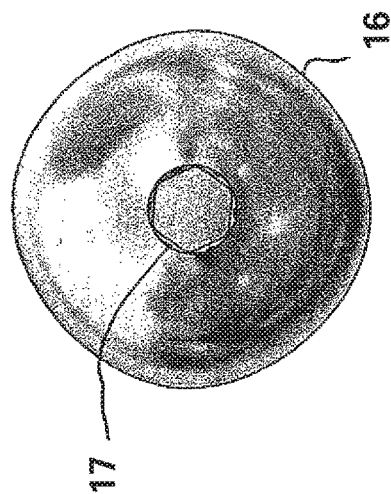

FIGS. 5A, 5B show an exemplary acetabular ball 16, which includes the threaded hole 36 that receives the second threaded portion 30 of the threaded stem 14 therein. As described above, the depth of the hole 36 may be greater than a length of the second threaded portion 30 of the threaded stem 14. This would help to ensure that the acetabular ball 16 was secured firmly with the threaded stem 14 when the hole 36 engaged the shoulder 32. The threaded stem 14 will come in different sizes—lengths to allow for adjustability of the position of the ball within the system. In other words, provision of the threaded stem 14 in different lengths allows for inward and outward adjustment on the stem, which in turn allows the ball to be moved medially or laterally in and out of the joint as deemed appropriate. Thus, if the ball 16 needs to be spaced further away from the inside surface 74 of the insert 26 an appropriate sized stem 14 would be selected and used to achieve the proper spacing. Also, as shown in FIG. 5B the acetabular ball 16 may have an hexagonal socket 17 or the like defined in a surface thereof opposite to the hole 36 so that a hexagonal wench or other appropriate tool can be fitted to the socket for tightening the ball onto the second threaded portion 30 of the threaded stem 14. As a practical matter, the threaded stem 14 which interconnects the components of the acetabular cup arrangement 12 and the acetabular ball 16 may function as an artificial ligamentum teres ligament and will keep the joint pulled into the hip socket.

Figure 6B:
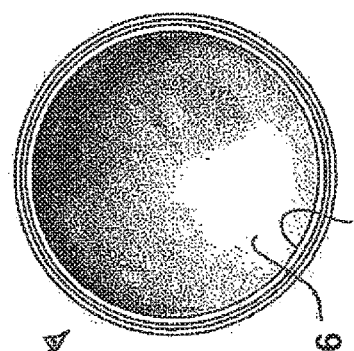
FIGS. 6A-6B show different views of a femoral cup that is part of the hip system shown in FIG. 1.
Figure 6A:
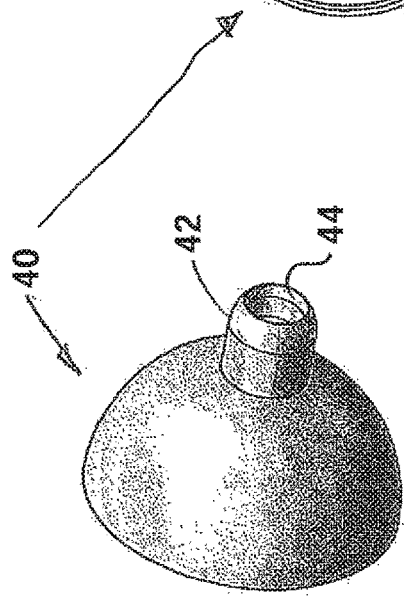
Figure 7B:
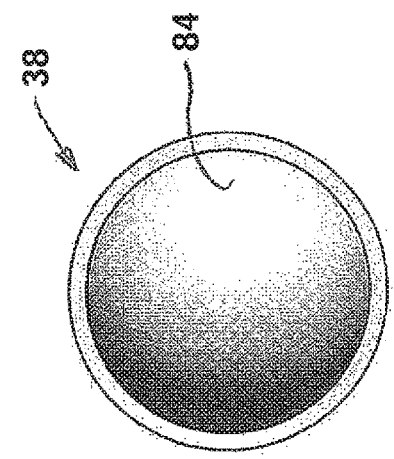
FIGS. 7A-7B show different views of an insert that can be used with the femoral cup is shown in FIGS. 6A-6B.
Figure 7A:
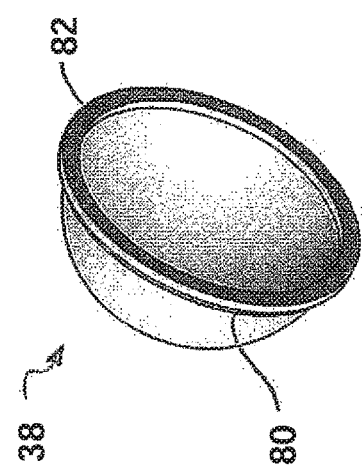

FIG. 6A shows a perspective view of the femoral cup 40, and FIG. 6B shows and end view of the femoral cup from the opposite side of that shown in FIG. 6A. The stem 42 is disposed on a distal portion of the cup 40, and as described above includes a female Morse taper 44. In other embodiments, a stem, such as the stem 42, may be configured with a male Morse taper that would mate with a female Morse taper on a femoral stem. FIG. 6B shows an inside or proximal surface 76 of the femoral cup 40 and a circumferential lip 78 configured to engage with a lip 82 of the insert 38 (see FIG. 7A) with a snap-fit similar to the snap fit structure between the acetabular cup 24 and insert 26 discussed above. Particularly, a groove 80 is a circumferentially disposed around a lip 82 of the insert 38, and is configured to securely engage an annular recess defined in the lip 78 on the femoral cup 40. Again, other means may be provided to assure proper fitment between the cup 40 and the insert 38. An inside surface 84 of the insert 38 provides an articulating surface for the acetabular ball 16. As described above in conjunction with FIG. 1, the femoral cup 40 and the insert 38 form a femoral cup arrangement 18, which is configured for attachment to the femoral stem 20. For example, the stem 20 may be securely inserted into the intramedullary canal of a patient's femur, the femoral cup 40 secured to the neck 46 of the femoral stem 20, and then the insert 38 secured to the femoral cup 40.

Figure 8A:
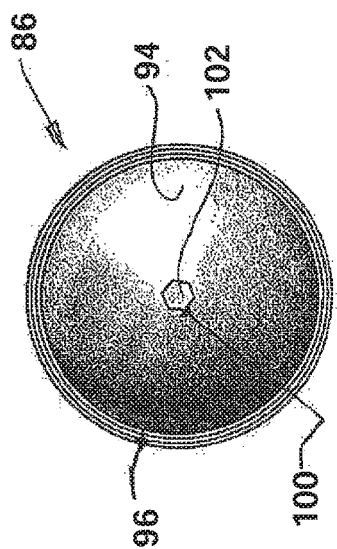
FIGS. 8A-8B show different views of an alternative embodiment of a femoral cup described herein.
Figure 8B:
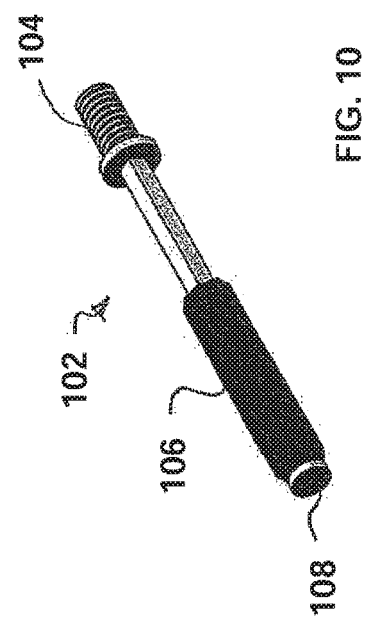
Figure 9:
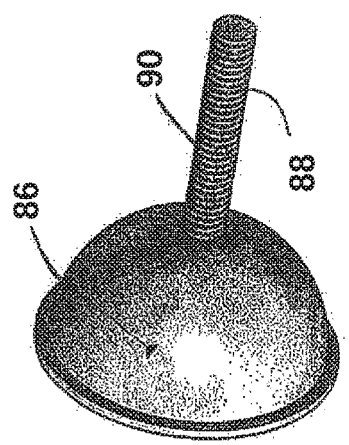
FIG. 9 shows an alternative embodiment of a femoral stem described herein.

In other embodiments, a femoral cup, such as the femoral cup 40, may be configured to attach to a femoral stem through a fixation mechanism other than a Morse taper. For example, FIG. 8A shows a femoral cup 86 that includes an elongated member 88 extending outward from a central portion of the cup and projecting in the distal direction thereof. In the embodiment shown in FIG. 8A, the elongated member 88 is a threaded rod that includes male threads 90 which, as described in more detail below in conjunction with FIG. 9, is configured to attach the cup 86 to a femoral stem 92. Although an elongated member such as the threaded rod 88 may be integrally formed with the cup 86, it may also be a separate threaded stem, similar to the threaded stem 14 shown in FIG. 1. Differing from the threaded stem 14, the threaded rod 88 includes only one set of threads 90, and they extend in a distal direction only. FIG. 8B shows an inside or proximal surface 94 of the femoral cup 86 and a circumferential lip 96 configured to engage with engage an insert, such as the insert 38 described above.

FIG. 9 shows an alternative version the femoral stem 92, which includes a threaded hole 98 configured to receive the threaded rod 88 of the femoral cup 86, but does not include a neck such as the neck 46 of the femoral stem 20 shown in FIG. 1. Whether the threaded rod 88 is integral to or separate from the cup 86, it may include an end 100, see FIG. 8B, having a socket 102 or the like configured to receive a tool for facilitating securement to the stem 92. Similar to the distal end 64 of the threaded stem 14, the socket 102 may be a hexagonal, square, torque or hexalobular socket or the like. Although the stems 20, 92 are illustrated without striations, porous coating, or a platform at their respective proximal ends, other embodiments may include one or more of these features, as well as different geometric configurations, depending on the patient's requirements and preferences.

Figure 10:
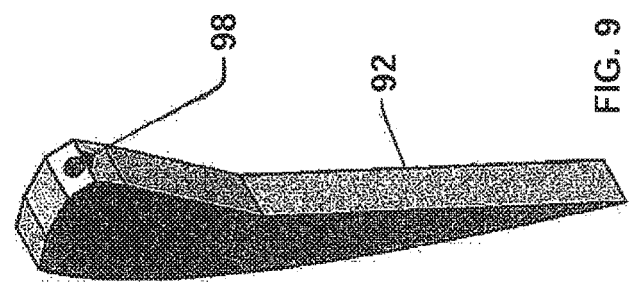
FIG. 10 shows an insertion tool that can be used for inserting at least a portion of the acetabular cup arrangement into a patient's acetabulum.

FIG. 10 shows a tool 102, which can be used, for example, to insert the anchor cup 22 into a patient's acetabulum. A threaded portion 104 is configured to engage the threads inside the hole 54 of the anchor stem 34, see, e.g., FIG. 2B. A handle 106 allows a surgeon to firmly grip the tool 102, and an impact surface 108 is provided so that a mallet can be used to impact the tool 102 to drive the stem 34 of the anchor cup 22 securely into the acetabulum. A tool, such as the tool 102, may be made from any of a variety of materials, including stainless steel, or any other material effective for the intended use of the tool 102. Similarly, components of the hip system 10 and other embodiments described herein may be made from any of a number of known materials which are appropriate/compatible for use with humans, such as titanium alloys, cobalt-chromium alloys, ultra-high-molecular-weight polyethylene, cross-linked polyethylene, alumina ceramics, zirconia ceramics, and combinations thereof just to name a few.

Figure 14:
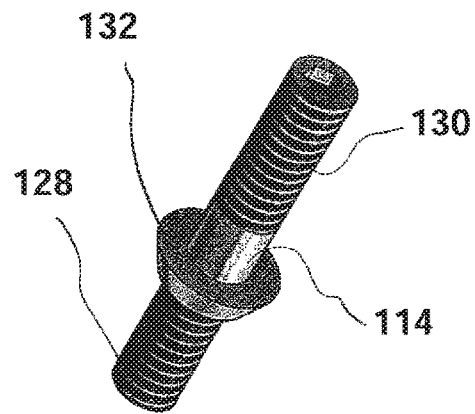
FIG. 14 shows a fastener that can be used to connect components of the acetabular cup arrangement shown in FIG. 11.
Figure 15A:
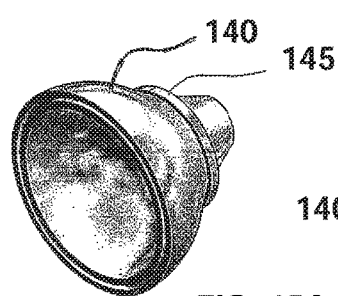
FIGS. 15A, 15B a femoral cup that is part of the hip system shown in FIG. 11.
Figure 15B:
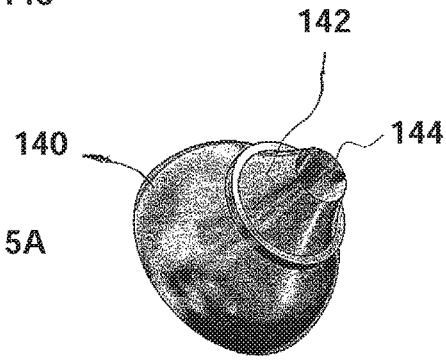

FIG. 11 shows an exploded view of a reverse prosthesis hip system 110 in accordance with another exemplary embodiment described herein. This system 110 is similar to the system 10 shown in FIG. 1 in that it is a reverse configuration system and includes an acetabular cup arrangement 112, a threaded stem 114, an acetabular ball 116, a femoral cup arrangement 118 and a femoral stem 120, and some of the same components may be used in both embodiments, e.g., the acetabular ball 116 may be the same as acetabular ball 16, insert 138 of the femoral cup arrangement 118 may be the same as insert 38 of the femoral cup arrangement 18, femoral stem 120 may be the same as femoral stem 20, etc. However, there are important differences discussed below. Additionally, FIGS. 12A-12C show different views of an anchor portion of an acetabular cup arrangement that is part of the hip system shown in FIG. 11, FIGS. 13A-13C show different views of a polymeric insert portion of the acetabular cup arrangement shown in FIG. 11, FIG. 14 shows a threaded stem 114 that can be used to connect components of the acetabular cup arrangement shown in FIG. 11, and FIGS. 15A, 15B show a femoral cup that is part of the hip system shown in FIG. 11.

One difference of the system 110 is that the acetabular cup arrangement 112 includes only two components, i.e., an anchor portion 122 that also functions as an acetabular cup and an insert 126 that connects directly to the anchor portion 122 via a snap fit arrangement or other or appropriate means. In other words, the acetabular cup arrangement 112 eliminates the separate acetabular cup 24 used in system 10, and thus is simplified and more cost efficient in comparison to the acetabular cup arrangement 12.

Figure 12A:
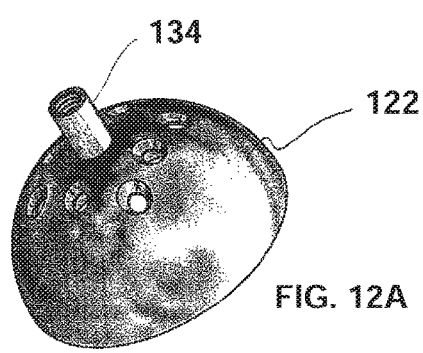
FIGS. 12A-12C show different views of an anchor portion of an acetabular cup arrangement that is part of the hip system shown in FIG. 11.
Figures 12B, 12C:
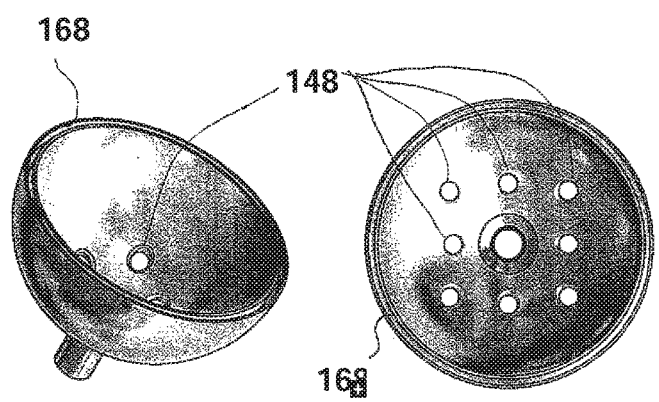

Referring to FIGS. 12A-12C, the anchor portion 122 may have a similar structure to the first-anchor portion 22 in the system 10, including a stem 134 which projects from the center of a distal surface of the portion 122 and is internally threaded, a plurality of openings 148 that surround the stem 134 and through which the bone screws 137 may extend into the patient's acetabulum. This stem 134 is open at both ends rather than closed like the projecting end of the stem 34, which may help in securing the stem 134 to the patient's acetabulum. Alternatively, the stem 134 may be omitted, such as on the anchor portion 122 shown in FIG. 11, in which case the first threaded end 128 of the threaded stem 114 may be directly connected to the patient's acetabulum. The non-projecting end of the stem 134 and the holes 148 may be countersunk such as shown so that the holes 148 may flushly receive tapered heads of the bone screws 137 and the stem end may flushly receive a tapered flange 132 at an intermediate portion of a threaded stem 114 discussed further below, and whereby the screw heads and intermediate portion of the stem 114 will favorably not degrade the concavity of a surface of the insert 126 that engages same. A self-centering bone screw guide (not shown) may be used to drill pilot holes including the countersunk properties. Of course, holes 48 in the anchor portion 22 of system 10 may also be countersunk. Additionally, because the anchor portion 122 connects directly to the insert 126 in this embodiment, the anchor portion is also provided with a circumferential, annular recess 168 to which a circumferential, annular projection 166 provided with the insert 126 may be securely fitted similarly to the connection between the acetabular cup 24 and insert 26 of the system 10 discussed above. Again, other appropriate means for having the insert 126 securely connected and fitted to the anchor portion may be provided alternatively or in addition to the projection 166 and recess 168.

Like the anchor portion 22 in system 10 the anchor portion 122 comes in various sizes and the largest size suitable for the patient is typically selected and fixed to the patient's acetabulum using bone screws 137, by configuring the anchor portion 122 for bone ingrowth, e.g., it may be porous coated, coated with hydroxyapatite, plasma-spray coated, it may have other geometric configurations, or it may have some combination of one or more of these, etc.

Figure 13A:
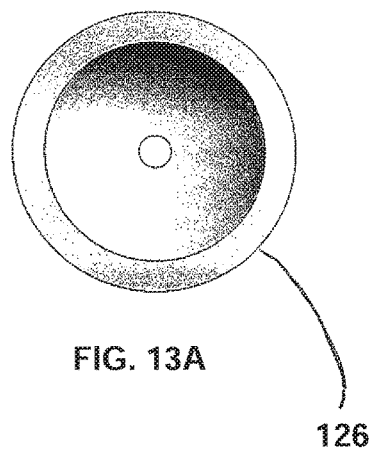
FIGS. 13A-13B show different views of a polymeric insert portion of the acetabular cup arrangement shown in FIG. 11.
Figure 13B:
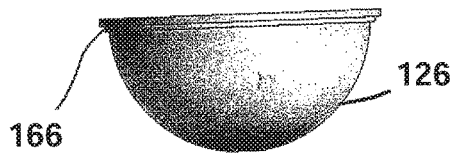
Figure 13C:
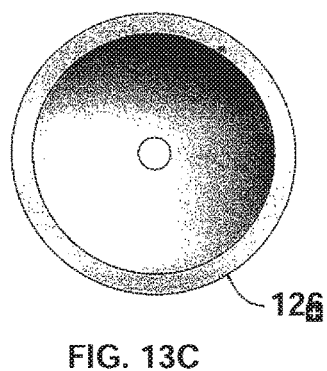
FIG. 13C is similar to FIG. 13A but shows a different sized insert.

Referring to FIGS. 13A-13C, the insert 126 may be made of materials such as high density polyethylene (HDPE), high molecular weight polyethylene (HMWPE), other suitable polymers, or other suitable materials. The insert 126 will also come in different sizes so that a most appropriate sized insert may selected for each patient, e.g., as shown in FIGS. 13A and 13C a flange having the annular projection 166 thereon may come in different widths, a wall thickness of the insert may be different for the different sizes, etc. Thus, the inner diameter of the acetabular cup arrangement 112 will be adjustable by various thickness sized liners which will increase and decrease the inner diameter of the cup to a size which is most appropriate for each patient. Generally, the insert 126 will have an increased wall thickness in comparison to insert 26 in system 10 because the separate acetabular cup 24 is eliminated and the insert 126 is provided with various wall thicknesses for adjustability, and such increased wall thickness may increase the life expectancy of the system as it will generally take longer to wear down the insert 126 having a larger wall thickness, and may help to reduce overall wear and tear on the patient's hip joint. The adjustability in the thickness of the insert 126 will also permit greater adjustability of the joint, thus ensuring stabilization and proper fitness.

Referring to FIG. 14 there is shown an enlarged view of the threaded stem 114. The stem is quite similar to the threaded stem 14 of the system 10 in that it includes first and second threaded portions 128, 130 and a non-threaded intermediate portion between the two threaded portions. The threaded stem is different from the stem 14 in that it may include an annular flange 132 which projects outwardly therefrom rather than the shoulder 32 included with the stem 14. Also, one face of the flange 132 may be tapered such that the diameter thereof is reduced as it extends toward the first threaded end 128, and whereby such face of the flange will flushly engage with the countersunk opening in the anchor portion 122 that extends into the stem 134 as discussed above. Further, if the anchor portion 122 does not include the projecting stem 134, such as shown in FIG. 11, the end of the first threaded portion of the stem 114 should be pointed for facilitated attachment to the patient's acetabulum, and the threads should be suitable for attachment into the bone of the patient's acetabulum, rather than threads for being mated to threads within the stem 134. Again, the threaded stem 114 which interconnects the components of the acetabular cup arrangement 112 and the acetabular ball 116 may function as an artificial ligamentum teres and will keep the joint pulled into the hip socket.

Referring to FIGS. 15A, 15B there is shown a femoral cup 140 of the system 110. This femoral cup 140 is similar to the femoral cup 40 in the system 10, but has a tapered outer surface that seamlessly extends into a stem 142 at a narrow end thereof, which stem 142 has a recess 144 defined in the end thereof and configured to receive a Morse Taper type fastener therein. Additionally, an annular projection 145 is provided on the distal or outer surface thereof. Should the femoral cup have to be removed for some reason, the annular projection 145 could act as a gripping point for a retracting tool to be placed and to which suitable force could be applied for dislodging the cup 140 from the femoral stem 120. Of course, the annular projection 145 could be replaced and/or supplemented with equivalent structure such as an annular recess, the projection and/or recess need not be annular, but may include plural projections and/or recesses spaced around the circumference of the distal or outer surface thereof, etc.

The system 110 may also provide advantages in comparison to the system 10 in terms of repair and replacement. For example, with the system 10, in order to revise the inner diameter of the acetabular cup arrangement 12 it would be necessary to remove the ball 16, then the threaded stem 14, then the insert 26, then the bone screws 137, before being able to remove the acetabular cup 24 and replace it with another, appropriately sized cup 24, while the first/anchor portion 22 remains attached to the patient's acetabulum. With the system 110, however, once the ball 116 is removed the threaded stem 114 and bone screws 137 may remain attached to the patient along with the anchor portion 122, while the insert 126 could be disengaged from the anchor portion 122 and pulled off the threaded stem and replaced with another, appropriately sized insert 126. The facilitated revision process would also be much less traumatic for the patient.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined or substituted to form further embodiments of the invention. For example, in the system 10 of FIG. 1 the acetabular cup anchor portion may include a plurality of holes for receiving the bone screws wherein the holes have countersunk surfaces surrounding the holes so that the ends of the bone screws will be received flushly in the holes and surrounding countersunk surfaces, the central opening of the acetabular cup anchor portion will not include a countersunk surface surrounding the hole, but the central hole in the acetabular cup will have acountersunk surface surrounding the hole so that it will flushly receive a tapered surface of an annular flange provided on the acetabular stem such as the flange 132 in the system 110.

I claim:

1. A reverse hip prosthesis comprising:
   an acetabular cup anchor portion configured for insertion into an acetabulum of a patient and fixation therein, the acetabular cup anchor portion including a convex surface for engagement with the patient's acetabulum and a concave surface opposite to the convex surface;
   a plurality of first wearable inserts which are different from each other, and each of which may be selectively fixed to the acetabular cup anchor portion such that the first insert covers the concave surface of the acetabular cup anchor portion;
   an acetabular stem having a first threaded end configured to be fixed to the acetabular cup anchor portion and/or the patient's acetabulum and a second threaded end extending in an opposite direction to the first threaded end;
   an acetabular ball having a threaded recess therein which is attached to the second threaded end the acetabular stem;
   a femoral stem configured for insertion into an intramedullary femoral canal of the patient;
   a femoral cup attached to the femoral stem and having a concave surface which partially surrounds the acetabular ball; and
   a second wearable insert which is fixed to the femoral cup and covers the concave surface of the femoral cup;
   wherein the acetabular cup anchor portion is a largest size suitable for the patient's acetabulum, and the acetabular stem also functions as an artificial ligamentum teres.

2. The reverse hip prosthesis according to claim 1, wherein the acetabular cup anchor portion includes a projecting stem which projects from the convex surface thereof, the projecting stem being hollow with an internal threaded surface that securely receives the first threaded end of the acetabular stem therein, and the projecting stem being configured to be fixed to the patient's acetabulum.

3. The reverse hip prosthesis according to claim 2, wherein the projecting stem is open at opposite ends thereof.

4. The reverse hip prosthesis according to claim 1, wherein the acetabular cup anchor portion or each of the first wearable inserts includes a recess at a circumference of an end opening thereof and the other of the acetabular cup anchor portion or each of the first wearable inserts includes a projection at a circumference of an end opening thereof which securely engages in the recess.

5. The reverse hip prosthesis according to claim 4, wherein the recess and the projection are annular in shape.

6. The reverse hip prosthesis according to claim 1, wherein the acetabular stem has a non-threaded portion or an annular flange disposed intermediate the first and second threaded ends, and the second threaded end is configured for being engaged by a tool which rotates the acetabular stem.

7. The reverse hip prosthesis according to claim 1, wherein the acetabular cup anchor portion has a central opening defined therein and a surface surrounding the central opening is countersunk, the acetabular stem has an annular flange disposed intermediate the first and second threaded ends, and one face of the annular flange is tapered in a direction extending toward the first threaded end such that the tapered face of the annular flange engages in the countersunk surface surrounding the central opening and an opposite face of the annular flange is flush with the concave surface of the acetabular cup anchor portion.

8. The reverse hip prosthesis according to claim 1, wherein the acetabular ball has another recess defined in a surface thereof opposite to the threaded recess and which is configured for being engaged by a tool which rotates the acetabular ball onto the acetabular stem.

9. The reverse hip prosthesis according to claim 1, wherein the femoral cup includes at least one of a projection and a recess on an outer surface thereof which is configured to be engaged by a tool for disconnecting the femoral cup from the femoral stem.

10. The reverse hip prosthesis according to claim 1, wherein one of the femoral cup and the second wearable insert includes a recess at a circumference of an end opening thereof and the other of the femoral cup and the second wearable insert includes a projection at a circumference of an end opening thereof which securely engages in the recess.

11. The reverse hip prosthesis according to claim 1, wherein the femoral cup and the femoral stem are connected by one of a Morse Taper and a threaded fastener.

12. A reverse hip prosthesis comprising:
an acetabular cup anchor portion configured for insertion into an acetabulum of a patient and fixation therein, the acetabular cup anchor portion including a convex surface for engagement with the patient's acetabulum and a concave surface opposite to the convex surface;
a plurality of acetabular cups which are different from each other, each acetabular cup including a convex surface for engagement with the concave surface of the and a concave surface opposite to the convex surface, and each of the acetabular cups may be selectively fixed to the acetabular cup anchor portion;
a first wearable insert which is fixed to the acetabular cup such that the first insert covers the concave surface of the acetabular cup;
an acetabular stem having a first threaded end configured to be fixed to the acetabular cup anchor portion and/or the patient's acetabulum, an intermediae portion that secures the acetabular cup to the acetabular cup anchor portion, and a second threaded end extending in an opposite direction to the first threaded end;
an acetabular ball having a threaded recess therein which is attached to the second threaded end the acetabular stem;
a femoral stem configured for insertion into an intramedullary femoral canal of the patient;
a femoral cup attached to the femoral stem and having a concave surface which partially surrounds the acetabular ball; and
a second wearable insert which is fixed to the femoral cup and covers the concave surface of the femoral cup;
wherein the acetabular cup anchor portion is a largest size suitable for the patient's acetabulum, and the acetabular stem also functions as an artificial ligamentum teres.

13. The reverse hip prosthesis according to claim 12, wherein the acetabular cup anchor portion includes a projecting stem which projects from the convex surface thereof, the projecting stem being hollow with an internal threaded surface that securely receives the first threaded end of the acetabular stem therein, and the projecting stem being configured to be fixed to the patient's acetabulum.

14. The reverse hip prosthesis according to claim 13, wherein the projecting stem is open at opposite ends thereof.

15. The reverse hip prosthesis according to claim 12, wherein each of the acetabular cups or the first wearable insert includes a recess at a circumference of an end opening thereof and the other of each of the acetabular cups and the first wearable inserts includes a projection at a circumference of an end opening thereof which securely engages in the recess.

16. The reverse hip prosthesis according to claim 15, wherein the recess and the projection are annular in shape.

17. The reverse hip prosthesis according to claim 12, wherein the intermediate portion of the acetabular stem is non-threaded or includes an annular flange disposed intermediate the first and second threaded ends, and the second threaded end is configured for being engaged by a tool which rotates the acetabular stem.

18. The reverse hip prosthesis according to claim 12, wherein the acetabular cup has a central opening defined therein and a surface surrounding the central opening is countersunk, the acetabular stem has an annular flange disposed with the intermediate portion, and one face of the annular flange is tapered in a direction extending toward the first threaded end such that the tapered face of the annular flange engages in the countersunk surface surrounding the central opening of the acetabular cup and an opposite face of the annular flange is flush with the concave surface of the acetabular cup.

19. The reverse hip prosthesis according to claim 12, wherein the acetabular ball has another recess defined in a surface thereof opposite to the threaded recess and which is configured for being engaged by a tool which rotates the acetabular ball onto the acetabular stem.

20. The reverse hip prosthesis according to claim 12, wherein the femoral cup includes at least one of a projection and a recess on an outer surface thereof which is configured to be engaged by a tool for disconnecting the femoral cup from the femoral stem.

* * * * *